United States Patent [19]
Clawson

[11] Patent Number: 5,857,966
[45] Date of Patent: Jan. 12, 1999

[54] METHOD AND SYSTEM FOR THE UNCONSCIOUS OR FAINTING PROTOCOL OF AN EMERGENCY MEDICAL DISPATCH SYSTEM

[76] Inventor: Jeffrey J. Clawson, 4649 Farm Meadow La., Salt Lake City, Utah

[21] Appl. No.: 827,265

[22] Filed: Mar. 28, 1997

[51] Int. Cl.[6] ............................. G06F 15/42; H04M 11/00
[52] U.S. Cl. ............................................................. 600/300
[58] Field of Search .................................... 600/300, 301; 128/897, 898, 903, 904, 905

[56] References Cited

U.S. PATENT DOCUMENTS

| | | | |
|---|---|---|---|
| 4,130,881 | 12/1978 | Haessler et al. | 364/900 |
| 4,237,344 | 12/1980 | Moore | 179/2 A |
| 4,290,114 | 9/1981 | Sinay | 364/900 |
| 4,489,387 | 12/1984 | Lamb et al. | 364/514 |
| 4,839,822 | 6/1989 | Dormond et al. | 364/513 |
| 4,858,121 | 8/1989 | Barber et al. | 364/406 |
| 4,945,476 | 7/1990 | Bodick et al. . | |
| 5,063,522 | 11/1991 | Winters | 395/51 |
| 5,065,315 | 11/1991 | Garcia . | |
| 5,072,383 | 12/1991 | Brimm et al. . | |
| 5,253,164 | 10/1993 | Holloway et al. | 364/406 |
| 5,255,187 | 10/1993 | Sorensen . | |
| 5,339,351 | 8/1994 | Hoskinson et al. | 379/45 |
| 5,348,008 | 9/1994 | Bornn et al. | 600/383 |
| 5,471,382 | 11/1995 | Tallman et al. | 364/406 |
| 5,513,993 | 5/1996 | Lindley et al. | 434/319 |
| 5,521,812 | 5/1996 | Feder et al. | 364/400 |
| 5,554,031 | 9/1996 | Moir et al. | 434/111 |
| 5,596,994 | 1/1997 | Bro . | |

Primary Examiner—John P. Lacyk
Assistant Examiner—Samuel Gilbert
Attorney, Agent, or Firm—Lloyd W. Sadler

[57] ABSTRACT

A method and system for receiving, processing and responding to emergency medical calls for patients who have fainted or are unconscious is described. A consistent, standard and systematic process is provided which in combination with adequate training, supervision and quality assurance serves to provide a method for gathering emergency medical information regarding providing emergency medical dispatch services to patients who are unconscious or have fainted, categorizing such information into various determinant levels for appropriate response, and for giving qualified emergency medical information to callers thereby permitting "zero time" response by those at the scene. By using this invention properly a dispatcher is guided through the interrogation of callers concerned with patients who are unconscious or have fainted, gathering critical information and giving the appropriate guidance to the caller. This invention specifically guides the dispatcher through the steps of the unconsciousness protocol, thereby identifying the degree of urgency of such complaints and appropriately dispatching emergency medical responders.

9 Claims, 5 Drawing Sheets

31 UNCONSCIOUS / FAINTING (NON-TRAUMATIC)

AMPDS v10.2 NAE

KEY QUESTIONS (701)

1. Is s/he diabetic? —————————————— ⬜ — 13
2. Does s/he have any heart problems?
3. Is s/he breathing normally?
4. (If unconscious initially) Is s/he still unconscious?
   (You go check - I'll stay on the line.)
   a. (If conscious) Is s/he alert (able to talk normally)?
      i. (If alert) Has s/he fainted more than once today?
   b. (If female age 12-50) Does she have any abdominal pain?

POST-DISPATCH INSTRUCTIONS (704)

a. Ensure ABCs
   1. Assure airway. ———————————— G1
   2. Verify breathing. ———————————— G4
   3. Treat for shock ———————————— G6
   4. No food or drink ———————————— G9
b. If her/his condition worsens in any way, call me back immediately for further instructions
c. Stay on the line with caller if her/his condition seems unstable or is worsening
d. If s/he is on any medications please get them out for the paramedics. Write down the name and phone number of her/his doctor. Put any family dogs away. Can someone meet the paramedics please?

DETERMINANTS (702) / RESPONSES

A
1. Single fainting episode and alert (age < 35)    1
2. Near fainting episode and alert (age < 35)      2

C
1. Single or near fainting episode and alert (age ≥ 35)    1
2. Multiple fainting episodes                              2
3. Females with abdominal pain (age 12-50)                 3
4. Conscious with abnormal breathing                       4
5. Cardiac history                                         5

D
1. Unconscious (at end of interrogation)    1
2. SEVERE RESPIRATORY DISTRESS              2
3. Not alert                                3

*This section is for user-defined responses and modes only.*

---

31 UNCONSCIOUS / FAINTING (NON-TRAUMATIC)

DEFINITIONS — AXIOMS — RULES — LAWS

Causes of Sudden Unconsciousness (705)

- Cardiac arrest
- Diabetic Problems
- Fainting (syncope)
- Head injury
- Heart Attack
- Hypovolemic Shock
- Intoxication
- Irregular heart rhythm
- Overdose: poisoning, drugs
- Respiratory insufficiency
- Seizures
- STROKE

SEVERE SEVERE RESPIRATORY DISTRESS, Classification (706)

- Extreme breathing difficulty
- Making "funny noises"
- Retractive breathing
- Turning blue

Rules (707)

1. An unconscious person in whom breathing cannot be verified by a 2nd party caller is considered to be in cardiac arrest until proven otherwise
2. When appropriate, stay on the line with the caller when the patient is still unconscious to ensure ABCs until responders arrive

Axioms (708)

1. Fainting implies a state of unconsciousness that the patient has "come to" from. While this is generally less serious than prolonged unconsciousness, it does not imply a benign condition and should be medically evaluated
2. Statistically, the most common cause of sudden unconsciousness reported to dispatch is seizure
3. The Chief Complaint and the main associated symptoms (such as ) are sometimes reversed by the caller in ectopic pregnancy and aneurysm cases
4. If the caller doesn't seem to understand "Is s/he alert," ask "able to talk," then "awake" or even "with the program," "making sense," or a more descriptive phrase
5. "Funny noises" reported by the caller generally means the patient is unconscious with an uncontrolled airway and often represents agonal (dying) respirations at the beginning of a cardiac arrest
6. Agonal respirations can be confused with "still breathing" before they fade away during an arrest. Unconscious patients should be re-checked frequently. See PDI "Breathing" (G2)

FIG. 7

METHOD AND SYSTEM FOR THE UNCONSCIOUS OR FAINTING PROTOCOL OF AN EMERGENCY MEDICAL DISPATCH SYSTEM

SPECIFICATION

This application is based on Provisional Application Ser. No. 60/014,741, which was filed on Mar. 29, 1996, and priority is claimed thereto.

SOFTWARE APPENDIX

This specification includes a software appendix which includes an enabling description of one preferred embodiment of the design and implementation of the process of the invention in the computer software alternative embodiment of the invention. This appendix is produced herein to provide programmers of ordinary skill in the arts of emergency medical procedures and computer programming all information necessary to enable their coding, use and practice of the software embodiment of the invention. In other embodiments of the invention, the inventive concept may be implemented in other computer code, in computer hardware, in other circuitry, in a combination of these, in a reference card or flowchart format not involving computer technology at all, or otherwise. An alternative preferred embodiment of the invention is a reference card format. The software appendix is hereby incorporated by reference in its entirety and is considered to be a part of the disclosure of this specification.

BACKGROUND OF THE INVENTION

1. Field of the Invention

This invention relates to methods and systems for processing and responding to emergency medical inquiries. Specifically, this invention relates to the process or method of managing the dispatch of emergency medical care to callers or patients with complaints related to unconsciousness or fainting. Providing adequate emergency medical care presents several critical challenges to medical care providers. These challenges include: the proximity to the care provider, the time required for help to arrive, the identification of the criticality of the emergency, the appropriate level of care provided, the variances in training of emergency medical dispatcher personnel, and limited nature of emergency care resources. This invention addresses these challenges by providing a consistent and proven system for: First, gathering necessary medical complaint information from emergency medical inquiry callers and providing emergency verbal instructions to individuals at the scene. Second, prioritizing the complaint to determine the criticality of the emergency. Third, assisting dispatched responders to be prepared for each emergency situation. Fourth, advising those on the way to provide care at the scene of specific problems or potential hazards. When used correctly this invention decreases the effective response time, while increasing the professionalism and control of emergency medical dispatchers, increases the accuracy and appropriateness of patient interrogation and well as the quality of gathered information, reduces the number of multiple unit responses thereby reducing the risk of emergency medical vehicular collisions, improves patient care, reduces burn-out and stress of dispatchers by improving their quality of training, decreases the risk of responder injury or mistake by providing responders with improved knowledge of the situation, and provides an means for continuously improving the quality of emergency patient care.

While being included within a greater invention that addresses all of the above issues, this invention specifically addresses the unconscious or fainting medical emergency protocol or procedure. Unconsciousness and/or fainting constitute some of the most common emergency medical calls. Moreover, such calls often are the first indication of extremely serious medical problems. Accurate, efficient and systematic responses to these calls can and does make the difference in the successful resolution of such incidents. This invention specifically addresses the emergency medical problems and the procedures for dealing with patients who are having episodes of unconsciousness and/or fainting, especially as such episodes are related to the dispatch of emergency medical responders.

2. Description of Related Art

It is desirable to provide a systematic and standardized method for responding to emergency medical requests. Although in the related art some attempt has been made to address the problem of medical care assessment, the related art does not address the specific problems of emergency dispatcher response to medical problems related to unconsciousness or fainting. Rather related art approaches describe the following. A process of helping patients assess their health, select appropriate health care, and guide such patients to an appropriate level and type of care. An automated medical history taking system and a technique wherein selected branch paths through a question repertory are provided. A method and apparatus for coordinating the actions of two or more medical teams, especially for instructional purposes. An expert system for providing suggested treatments for a patient with physical trauma. A medical payment system that incorporates computer technology in the storage, retrieval and processing of patient data and insurance claims. A knowledge base containing medical/pathological information on various diseases. A hospital computerized system for entering information pertinent to a patient's stay in the hospital. An expert computer system for processing medical claims. An interactive computerized apparatus and method for presenting medical information for diagnosis and study of disease. An automated and interactive positive motivation system to send a series of motivational messages and/or questions to a client to change or reinforce a specific behavioral problem. An artificial intelligent expert system. A rapid response health care communications system for providing rapid and reliable health services to patients located within or outside a health care facility.

For general background material, the reader is directed to U.S. Pat. Nos. 4,130,881, 4,237,344, 4,489,387, 4,839,822, 4,858,121, 4,945,476, 5,063,522, 5,065,315, 5,072,383, 5,253,164, 5,255,187, 5,471,382, and 5,596,994. Each of the above references is hereby incorporated by reference in its entirety for the material disclosed therein.

SUMMARY OF THE INVENTION

It is desirable to provide a system for emergency medical dispatch of health care services that provides the dispatcher a systematic method of interrogation of callers, where inquiries and instructions are pre-scripted, thus eliminating the variability due to different skills of the individual dispatchers and the need for the dispatcher to attempt to recall the appropriate inquiries and instructions each time a call is received. Furthermore, it is desirable to provide a system for emergency medical care dispatch that improves the accuracy and appropriateness of patient interrogation and resulting response generation. Such a system can formalize the roll of the emergency medical dispatcher as part of the professional chain of patient care. It is also desirable to have a method for communicating with medical response teams such that multiple unit and light-and-siren responses are reduced, thereby reducing the collision risks to emergency vehicles and preserving the limited emergency response resources. It is desirable to provide a medical dispatch system that improves patient care by improving the accuracy and usefulness of gathered information, thereby reserving paramedic teams for the most critical emergencies. It is desirable to have a medical dispatch system that reduces dispatcher burn-out and stress by improving information relayed to field responders while simultaneously providing such responders with increased safety awareness and knowledge of the field situation.

Accordingly, it is the primary object of this invention to provide a medical dispatch system that is designed to guide the medical dispatcher through the interrogation, obtaining vital patient information regarding calls concerning episodes of unconsciousness and/or fainting. Including but not limited to unconsciousness and fainting situations involving diabetic victims, heart attack victims, drug problems, stroke victims, and pregnancy problems.

Another object of this invention is to provide a cross-referenced scripted set of instructions to be given by the dispatcher to the caller in an unconscious or fainted victim medical emergency situation.

It is a further object of this invention to provide a method of determining the criticality of such a medical emergency and communicating such level of criticality to the response personnel.

It is a still further object of this invention to provide a method for gathering and communicating information concerning the emergency situation at the field location to the response personnel and the emergency medical callers.

A further object of this invention is to improve the quality, efficiency and usefulness of the information received to and communicated by emergency medical dispatchers thereby improving the quality of emergency medical services provided to patient before, during and after the arrival of emergency medical technicians.

These and other objects of this invention, which will be clear to those of ordinary skill in the art upon review of this patent specification and claims, are achieved by an invention which permits a systematic gathering of patient information, with a set of scripted instructions and with guidance for relaying information to the field emergency personnel. The method and system of this invention is currently envisioned in two equally preferred embodiments. First, a set of cross referenced cards with scripted questions, instructions and categorizations is provided. Second, a computerized process is provided with software controlling the access and reference points to a computerized database of emergency medical inquiries and instructions is provides. Each preferred embodiment incorporates the same essential method of this invention, though each has its own particular advantages.

BRIEF DESCRIPTION OF THE DRAWINGS

FIG. 7 depicts the preferred embodiment of the flip cards used as one embodiment of this invention, which shows the steps of the unconscious/fainting protocol of the flip card deck embodiment of the invention.

DETAILED DESCRIPTION OF THE INVENTION

Figure 1:
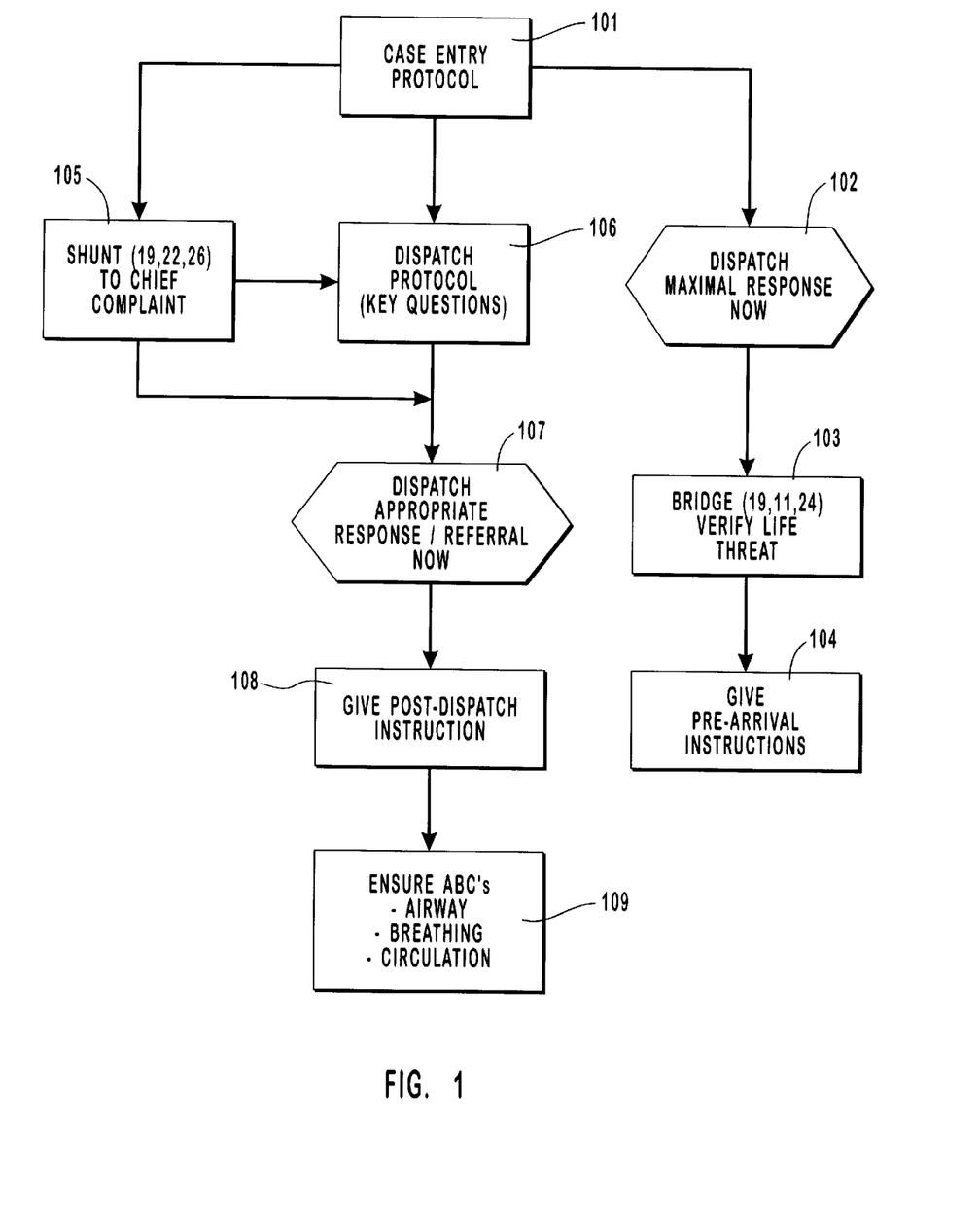
FIG. 1 depicts the principle elements of the complete system in which the preferred embodiment of the invention operates and the relationship of the elements of system to each other, and serves to put this invention in the context of the complete system.

This invention provides a method, system and an apparatus for receiving, processing and communicating emergency medical information, specifically related to medical problems related to unconsciousness and/or fainting, enabling an assessment of the critical or "key" information by trained emergency medical dispatch personnel. Sudden unconsciousness can be caused by a wide variety of different and serious medical emergencies. Such causes include: cardiac arrest, diabetic problems, fainting, head injury, heart attack, hypovolemic shock, intoxication, irregular heart rhythm, overdose, poisoning, drugs, respiratory insufficiency seizures and stroke. When the invention is properly employed the initial interrogation of the caller or patient will have previously provided the emergency medical dispatcher critical patient information which has indicated that the patient is most likely suffering from one or more episodes of unconsciousness or fainting. This information is applied in this invention which leads the dispatcher through a scripted interrogation, gathering additional related information, categorizing the problem by assigning a determinant value establishing the criticality of the problem, and then providing appropriate scripted established emergency medical instruction to the individuals on the scene. FIG. 1 shows the complete system in which the invention operates in its best mode. The process of managing emergency medical dispatchers, the information they require and the information they give is detailed in FIG. 1. The case entry protocol 101 provides the initial steps through which the all emergency callers or patients are taken to provide symptom information and to access medical information. The purpose of the case entry protocol 101 is to receive sufficient information to permit the dispatcher to identify the caller's chief complaint. This critical information received during the primary interrogation 101 includes a description of the problem (or the patient's complaint), the patient's age and the status of consciousness and breathing. This information is also referred to as "the four commandments of emergency medical dispatching." If the dispatcher receives information that the patient is unconscious and not breathing (or unconscious and breathing is uncertain or conscious but not breathing where the failure to breath has been verified), for whatever reason, a maximal response 102 is sent immediately, before continuing with any further interrogation or instructions, and the caller is told to stay on the line for further instructions. A maximum response dispatch 102 may include such resources as emergency medical technicians, ambulances, paramedics, and other appropriate medical care givers. The life threat is then verified 103 and pre-arrival instructions are given 104. These pre-arrival instructions 104 include six treatment sequence scripts covering Arrest, Choking, and Childbirth. Instructions 104 are given to guide the caller through CPR, the Heimlich Maneuver, or emergency childbirth procedures. In many cases, the result of properly conveyed instructions is a more viable patient by the time field personnel arrive. Should the dispatcher learn that the patient is breathing, but the dispatcher lacks sufficient information to directly go to the Key Questions of the Dispatch Protocol 106, the dispatcher is shunted 105 to additional interrogations whose purpose is to give the dispatcher the necessary information to ascertain the caller's chief complaint while focusing on heart problems, industrial/machinery accidents and/or general sick person issues. Once the dispatcher has enough information to have identified the caller's chief complaint, the dispatcher is taken to the Dispatch Protocol 106 where additional interrogations are performed to complete "key questions." This secondary interrogation 106 typically takes approximately 30 seconds and tends to focus on the specific or chief complaint of the caller. This secondary interrogation, or Dispatch Protocol 106, provides a more orderly and closer view of the patient so that the pre-hospital care provided is appropriate and in keeping with the severity of the injury or illness. The heart of this invention concerns the secondary interrogation 106 for the unconscious/fainting protocol. During this step 106 the dispatcher will match the symptoms, or combination of symptoms, discovered through interrogation and send the appropriate response 107. The appropriate response 107 is determined through a system of assigning determinant levels and numbers, from A2 generally less serious to D1 generally very serious. When the dispatcher identifies a determinant in one of the four levels (Alpha-A, Bravo-B, Charlie-C, and Delta-D) the response configuration (emergency vehicles and the mode of response) is dispatched as indicated by the response protocol. After the responders (field emergency medical caregivers) has been sent, the dispatcher remains on the telephone with the caller to give instructions 108 regarding what to do, and what not to do, prior to the arrival of the responders. This information is taken from the "Post-Dispatch Instructions" section of the protocols and provided whenever possible and appropriate. A main purpose of these "Post-Dispatch Instructions" 108 is to prepare the patient for and to expedite the field personnel's work at the scene. "Post-Dispatch Instructions" include such instructions as to collect the patient's medications, write down the name of the family doctor and put away pets. Each caller is also instructed to ensure 109 that the patient has an open airway, is breathing, is given nothing to eat or drink before responders arrive and, if necessary, how to treat for shock using the procedure given in the reference script for Airway, Breathing, and Circulation. Callers are routinely advised to "call back if the patient's condition worsens for further instructions."

Figure 2:
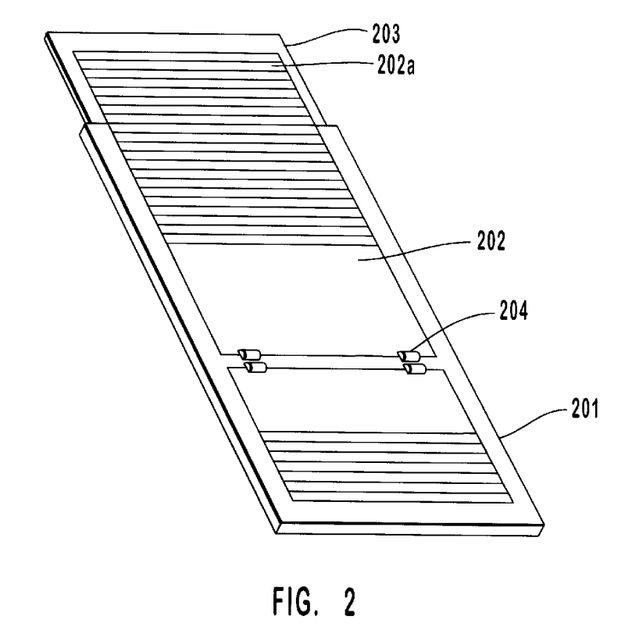
FIG. 2 depicts the flip card apparatus showing a preferred embodiment of the invention.

FIG. 2 depicts an embodiment of the flip card apparatus showing a preferred system for the use of the invention. One preferred embodiment of the invention involves the use of a flip card apparatus 201. The flip card apparatus 201 has the advantage of organizing the cards 202 so that the top, or bottom, label edge of each card can be seen by the user. Each card 202 is separately fastened into the apparatus with one or more fasteners 204. The steps embodying the elements of this invention, the entry protocol, are displayed on a top flap 203 and the first card 202a. Alternative embodiments of the card apparatus can be a deck of cards bound in a manner well known to those skilled in the art. In the current embodiment of the flip card apparatus there are sixty-four chief complaint cards, twelve pre-arrival instruction cards, two post-dispatch cards, one determinant classification card and two entry protocol cards. The cards are generally organized in pairs, with the top card providing the protocol questions, instructions, jump directions and determinant assignments. The bottom card provides information the dispatcher uses to improve the dispatcher's decision making process.

Figure 3:
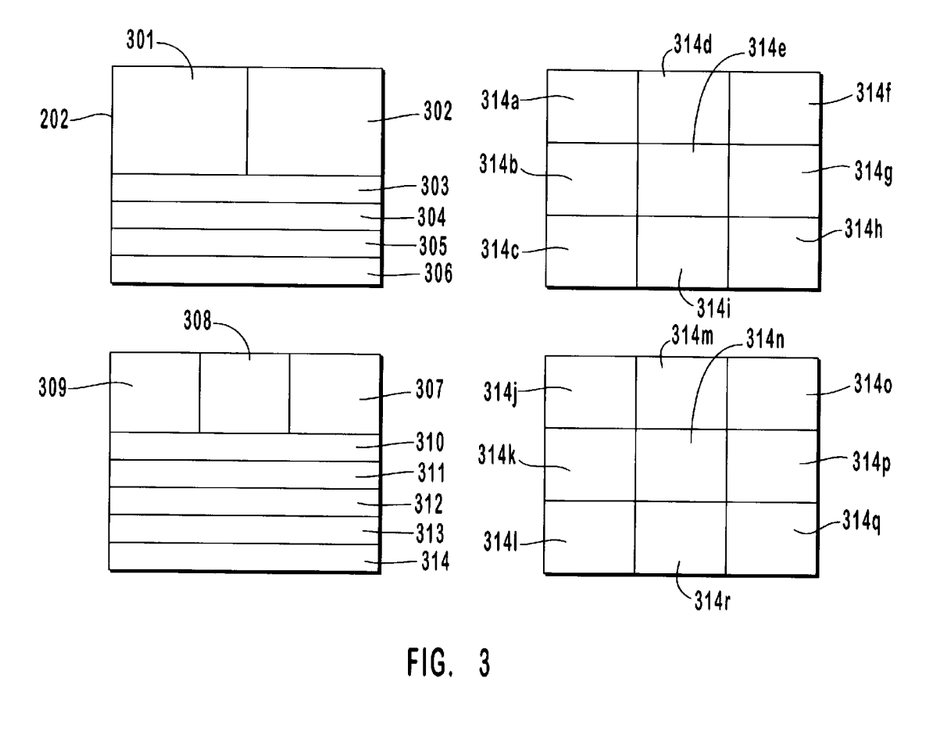
FIG. 3 shows a view of the sections of a typical flip card as used in the flip card apparatus embodiment of the invention.

FIG. 3 shows a view of the sections of a typical flip card, as used in the flip card apparatus embodiment of the invention. The typical flip card 202 is divided into logical sections for ease of use and consistency. A key question section 301 is provided as a script to the dispatchers to ensure that all key questions are asked in a calm, consistent, systematic manner. After all key questions are asked from the key question section 301, typically the dispatcher determines the appropriate determinant level. Sections A-Alpha 303, B-Bravo 304, C-Charlie 305 and D-Delta 306 are provided to aid the dispatcher in making the determinant designation. Each determinant level may have one or more sublevels. Generally, the most critical call is given a determinant level of D-Delta and the least critical call is given a determinant level of A-Alpha. The more critical the determinant level assigned to a call, the more medical resources and urgency may be applied to provide help. For example, an A-Alpha call will typically be responded to by emergency medical technicians and an ambulance proceeding to the patient under the safest method reasonably possible, while a D-Delta call will typically be responded to by the closest emergency medical technicians, an ambulance, paramedics, all who will proceed under the most urgent method possible. Sublevels may not indicate the criticality of the call, rather sublevel designations indicate the type of call, information often especially important to the dispatched medical team. After the determinant code is determined 303–306 the dispatcher is referred to the post-dispatch instructions section 302. The purpose of the post-dispatch instructions is to systematically prepare for and expedite the field personnel's job at the scene and to prevent further harm to the patient or others at the scene. The post-dispatch instruction section 302 includes such instructions as collecting the patient's medications, writing down the name of the family doctor and securing animals in the area. Each caller is also instructed, from the post-dispatch instruction section 302, to ensure that the patient has an open airway, is breathing, is given nothing to eat or drink before responders arrive, and, if needed, how to treat for shock using a reference script. Callers are also routinely advised to "call back if the patient's condition worsens for further instructions." Pre-arrival instructions 106 are provided on alternative cards 314, subsectioned as shown in FIG. 3 as 314 a–r. These pre-arrival instruction sections 314 provide scripted treatment sequences for arrest, choking and childbirth. These procedures, provided through sections 314, guide the caller through CPR, the Heimlich Maneuver or emergency childbirth procedures. Sections 307 to 314 provide important information to the dispatcher for the dispatcher's use in providing more educated responses. This information includes such information as categorizations of dangerous areas or injuries; types of injuries; symptoms; rules and axioms. Such information as is systematically provided to place the key questions of section 301, the determinant classifications of sections 303–306, and the post-dispatch instructions of section 302 into context for the dispatcher.

Figure 4:
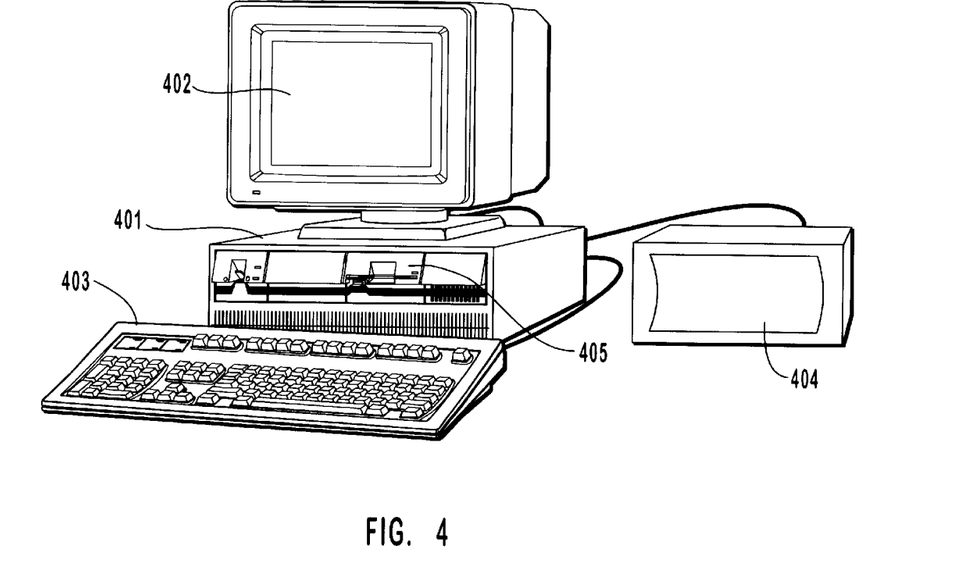
FIG. 4 shows a system diagram showing the components of a typical computer system used in the computerized embodiment of the invention.

FIG. 4 shows a system diagram of the components of a typical computer system used in the computerized embodiment of the invention. A second preferred embodiment of the invention is designed to operate in combination with a computer system using specially designed computer software incorporating the procedure of the invention. A typical computer system used in combination with software incorporating the invention includes a processing unit 401 to execute the instructions of the software; a display unit 402 to provide the means for providing the dispatcher with the prompts and information necessary to practice the invention; an input device 403 to provide the means for the dispatcher to interact with the software version of the invention; a storage device 405 for storage of the software and the files associated with the invention; and an output device 404 for printing reports and other information.

Figure 5:
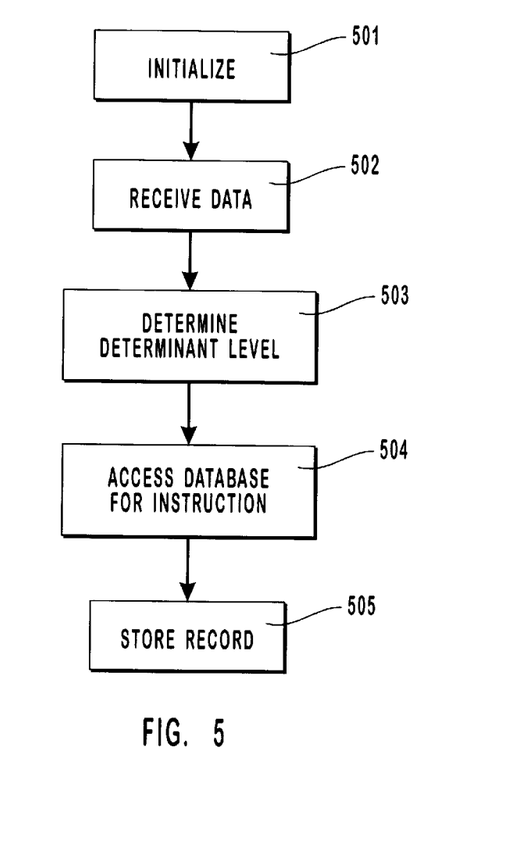
FIG. 5 shows a flow chart representation of the preferred top level steps of the invention.

FIG. 5 shows a process flow chart representation of the preferred top level steps of the invention. The software embodiment of the procedure of the invention is accomplished by performance of a number of procedural steps. First, the software is initialized 501. Data is received 502 following the request for information from the caller. As data is received 502, the determinant level is determined 503. Intermediate determinant levels are produced as information is received and processed, the final determinant level is only achieved after all necessary information is received and processed. A data base is accessed 504 to produce the appropriate instructions for communication with the caller. Records of the calls and queries are stored 505, for historical reports, for review of the dispatchers and for continued quality assurance control.

Figure 6:
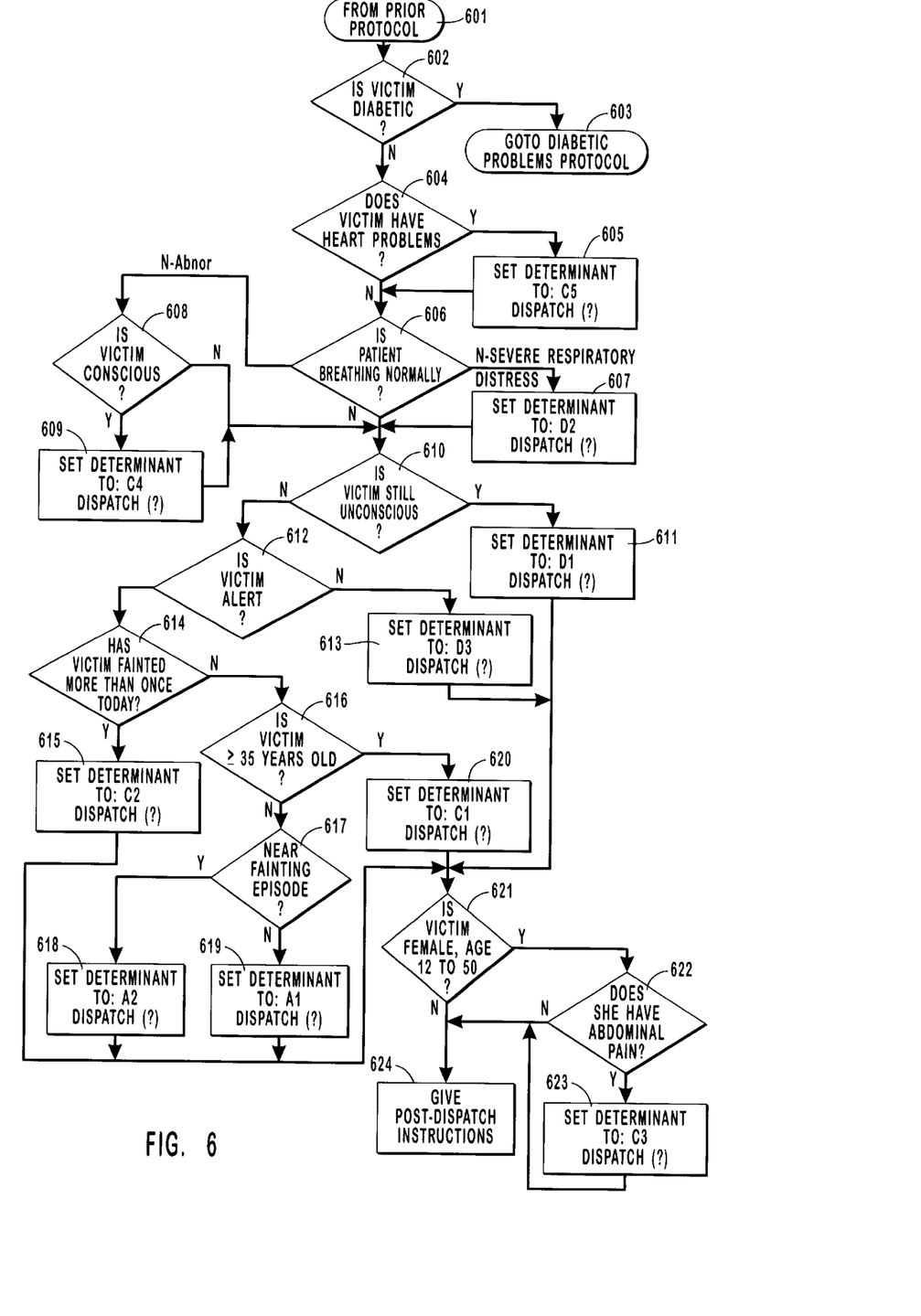
FIG. 6 depicts the detailed steps of the unconscious/fainting emergency medical protocol process constituting the preferred embodiment of the invention.

FIG. 6 depicts the detailed steps of the unconscious/fainting emergency medical protocol process of the preferred embodiment of the invention. Although the following steps of the process of the invention need not be accomplished in this specific order, alternative ordering of the steps of the invention are possible, this order of the steps of the process has been determined by the inventor to be the best mode of the invention. First, this protocol is reached by dispatchers after a prior protocol has been used to learn preliminary information 601. This prior protocol will provide, at a minimum, the following information: a description of the medical problem; the age of the patient; whether the patient is conscious; and whether the patient is breathing. This information, along with other information acquired during the process of this invention is used to assign determinants of criticality to the emergency as well to make important decisions as to the appropriate response and instructions which should be provided to the individuals at the scene. Next, an inquiry is made as to whether the victim is diabetic 602, if so the dispatcher is routed to the diabetic problems protocol 603. If not, information as to whether the victim has a history of heart problems 604, if so the determinant value is set to C5 and the dispatcher has the option of dispatching emergency medical responders 605. Next, the inquiry is made as to whether the patient or victim is breathing normally 606. If the victim is not breathing normally and is suffering severe respiratory distress then the determinant value is set to D2 and the dispatcher can optionally dispatch emergency medical responders. If the victim is not breathing normally, but is not in severe respiratory distress then the inquiry is made as to whether the victim is conscious 608, if so the determinant value is set to C4 and the dispatcher has the option of sending emergency medical responders. Next, an inquiry is made to learn if the victim is still unconsciousness 610, if so the determinant value is set to D1 and the dispatcher may dispatch emergency medical responders to the victim 611. If the victim is conscious, then the dispatcher inquires as to whether the victim is alert 612, if not, the determinant value is set to D3 and the dispatcher may dispatch emergency medical responders. If the victim is alert, the question of whether the victim has fainted more than once today 614, if so the determinant value is set to C2 and the dispatcher has the option of dispatching emergency medical responders 615. If the victim has not fainted more than once today, information from the prior protocol is utilized to establish whether the victim is greater than 35 years old 616, if so, the determinant value is set to C1 and the dispatcher has the option of dispatching emergency medical responders 620. If victim is less than 35 years old, then it is determined whether this was a "near fainting" episode 617. If it is a "near fainting" episode then the determinant value is set to A2 and the dispatcher has the option of dispatching emergency medical responders 618. If it is not a "near fainting" episode then the determinant value is set to A1 and the dispatcher has the option of sending the emergency medical responders 619.

Next, a test is made as to whether the victim is female and is between 12 and 50 years of age 621, if so, an inquiry is made as to whether the victim has abdominal pain 622 if she does then the determinant is set to C3 and the dispatcher has the option of dispatching emergency medical responders. If the victim is not female age 12 to 50 or does not have abdominal pain 622 then the dispatcher, next, gives the post-dispatch instructions 624. The post-dispatch instructions 624 include such instructions as ensuring that airway is maintained, breathing is verified, the victim is treated for shock, and that no food or drink is given to the victim. Also, the dispatcher typically tells the caller that if the victim's condition worsens in any way, the caller should call back immediately for further instructions. If the victim's condition seems unstable or is worsening the caller is instructed to stay on the line. If the victim is on any medications, the caller is instructed to get them out for the paramedics. The family doctor's name and phone number should be written down. The family dogs should be put away. And someone is requested to meed the paramedics.

Where the information can lead the dispatcher to more than one determinant value the dispatcher will typically assign the determinant value which indicates the most serious medical condition, but the dispatcher will communicate all relevant information to the emergency medical responders and for this reason all questions should be asked and answered unless clearly marked as qualified.

FIG. 7 depicts the preferred embodiment of the flip cards showing the steps of the unconsciousness protocol invention. Four key questions are shown in the "Key Questions" section 701. The "Determinants" section 702 is given to guide the dispatcher to the appropriate determinant level based on the responses given to the "Key Questions" 701. A "Go To" 703 column is provided to guide the dispatcher to the diabetic problems protocol when appropriate. Post-Dispatch instructions 704 are provided, guiding the dispatcher through emergency medical advice. A list of causes of sudden unconsciousness is provided 705. The classifications of severe respiratory distress is provided 706. Axioms 708 and rules 707 are provided to put the questions into context for the dispatchers.

It is to be understood that the above-described embodiments are merely illustrative of numerous and varied other embodiments which may constitute applications of the principles of the invention. Such other embodiments may be readily devised by those skilled in the art without departing from the spirit or scope of this invention and it is our intent that they be deemed within the scope of our invention.

I claim:

1. A method for managing the unconsciousness related medical call process of an emergency medical dispatch system, for dispatching medical assistance to patients needing such medical assistance, comprising the steps of:

(A) receiving a medical call on a telephone communication device regarding a patient needing medical assistance;
(B) inquiring if the patient is diabetic;
(C) inquiring if the patient has heart problems;
(D) inquiring if the patient is breathing normally;
(E) inquiring if the patient is still unconscious;
(F) inquiring if the patient is alert;
(G) setting an appropriate determinant value based on said inquiries
(H) dispatching medical personnel to the patient as determined by said appropriate determinant value.

2. A method for managing the unconsciousness related medical call process of an emergency medical dispatch system, as recited in claim 1, further comprising:
(I) giving instructions to the caller based on said set determinant value.

3. A system for managing the process of responding to related emergency medical calls related to unconscious patients, the system comprising:
(A) a telephone communication device on which an emergency medical call is received by a medical services dispatcher;
(B) a dispatcher guidance device for guiding the medical services dispatcher in gathering information from said emergency medical call;
(C) a first inquiry from said dispatcher guidance device whereby the medical services dispatcher is instructed to inquire as to whether the patient is diabetic;
(D) a second inquiry from said dispatcher guidance device whereby the medical services dispatcher is instructed to inquire as to whether the patient has heart problems;
(E) a third inquiry from said dispatcher guidance device whereby the medical services dispatcher is instructed to inquire as to whether the patient is breathing normally;
(F) a fourth inquiry from said dispatcher guidance device whereby the medical services dispatcher is instructed to inquire as to whether the patient is still unconscious;
(G) a fifth inquiry from said dispatcher guidance device whereby the medical services dispatcher is instructed to inquire as to whether the patient is alert; and
(H) a determiner for setting a level of criticality based on said first inquiry, said second inquiry, said third inquiry, said fourth inquiry and said fifth inquiry wherein said determiner is a basis for dispatching medical personnel.

4. A system for managing the process of responding to related emergency medical calls, as recited in claim 3, further comprising:
(I) an instruction from said dispatcher guidance device whereby the medical services dispatcher is instructed to instruct the caller based on said determiner value.

5. A system for managing the process of responding to related emergency medical calls, as recited in claim 3, wherein said first, second, third, fourth, and fifth inquiries are prompted by a computer system executing an emergency medical call management program.

6. A system for managing the process of responding to related emergency medical calls, as recited in claim 3, wherein said first, second, third, fourth, and fifth inquiries are prompted by an apparatus comprising one or more cross referenced cards being held together in a fixed order and organization by a binding frame.

7. A system for managing the process of responding to related emergency medical calls, as recited in claim 3, wherein said dispatcher guidance device further comprises:

(1) a plurality of cards;
(2) a fastener fastening said plurality of cards to said device; and
(3) a means for directing the dispatcher from one of said plurality of cards to others of said plurality of cards.

8. A method for managing the process for responding to an emergency medical call relating to a patient who is unconscious or who has fainted in a general purpose computer system comprising:
a central processing unit;
dynamic memory,
static memory,
a display device,
an input device,
an output device,
a mass storage device which contains
a number of emergency medical instruction records,
a number of medical information records,
a grouping of determinant codes,
a number of emergency medical inquiry reports,
the method comprising the steps of:
(A) displaying on the display device an instruction to inquire if the patient is diabetic;
(B) receiving on the input device data indicating whether the patient is diabetic;
(C) storing said received diabetic indicator data in the dynamic memory;
(D) displaying on the display device an instruction to inquire if the patient has heart problems;
(E) receiving on the input device data indicating whether the patient has heart problems;
(F) storing said received heart problem indicator data in the dynamic memory;
(G) displaying on the display device an instruction to inquire if the patient is breathing normally;
(H) receiving on the input device data indicating whether the patient is breathing normally;
(I) storing said received breathing normally data in the dynamic memory;
(J) displaying on the display device an instruction to inquire if the patient is still unconscious;
(K) receiving on the input device data indicating whether the patient is still unconscious;
(L) storing said unconscious data in the dynamic memory;
(M) displaying on the display device an instruction to inquire if the patient is alert;
(N) receiving on the input device data indicating whether the patient is alert;
(O) storing said patient alert data in the dynamic memory; and
(P) setting a dispatch code in computer dynamic memory for the dispatch of emergency medical care to the patient based on said stored received data as to whether the patient is diabetic, has heart problems, is breathing normally, in unconscious, or is alert.

9. A method for managing the process for responding to an emergency medical call, in a general purpose computer system, as recited in claim 8, further comprising displaying on the output device an instruction to give specific medical information to the caller.

* * * * *